United States Patent [19]

Cullis et al.

[11] 4,187,979
[45] Feb. 12, 1980

[54] METHOD AND SYSTEM FOR FRACTIONATING A QUANTITY OF BLOOD INTO THE COMPONENTS THEREOF

[75] Inventors: Herbert M. Cullis, Silver Spring, Md.; Evelyn E. Dorsey, Washington, D.C.; James H. De Vries, McHenry, Ill.

[73] Assignee: Baxter Travenol Laboratories, Inc., Deerfield, Ill.

[21] Appl. No.: 944,640

[22] Filed: Sep. 21, 1978

[51] Int. Cl.² ............................................. B04B 15/12
[52] U.S. Cl. .................................. 233/14 R; 233/26; 128/214 D
[58] Field of Search ................ 233/14 R, 14 A, 19 R, 233/19 A, 27, 26, 21, 22; 128/214 R, 2 F, 214 D

[56] References Cited

U.S. PATENT DOCUMENTS

| | | | |
|---|---|---|---|
| 3,655,123 | 4/1972 | Judson et al. | 233/21 |
| 3,967,777 | 7/1976 | Canevari | 233/19 R |
| 3,982,691 | 9/1976 | Schlutz | 233/21 X |
| 4,091,989 | 5/1978 | Schlutz | 233/27 X |

*Primary Examiner*—George H. Krizmanich
*Attorney, Agent, or Firm*—Henry W. Collins; Thomas R. Vigil; Paul Flattery

[57] ABSTRACT

The method, and system for carrying out the steps of the method, are utilized in taking whole blood from a supply of blood withdrawn from a donor or from a previously banked supply of whole blood in a container, centrifuging the blood in a centrifuge device to separate the whole blood into its components, and then collecting the components, namely red blood cells, white blood cells, platelets and plasma. The fractionation of the whole blood in the centrifuge device takes place in first, second and third separation chambers. The first chamber has a square shape and is positioned in the centrifuge device in a diamond position. Each corner of the first separation chamber has an opening. Whole blood is pumped into one side corner opening and red blood cells are withdrawn from the other side corner opening and returned to the container for recirculation through the first chamber. White blood cells, platelets and plasma are withdrawn from the upper corner opening and passed through the second chamber wherein white blood cells are separated by centrifugal force. The plasma and platelets are then withdrawn from the second chamber and passed through the third chamber wherein the platelets are separated from the plasma by centrifugal force. The plasma exiting from the third separation chamber is passed back into the bottom corner of the first chamber to cause a flow of plasma across the flow of whole blood and red blood cells to elute white blood cells and plateletstherefrom and to wash the red blood cells. By appropriate operation of electromechanically controlled clamps associated with tubing carrying the various blood components, plasma can be siphoned off into a plasma collection receptacle located outside the centrifuge device. After the red blood cells have been recirculated several times through the first separation chamber, the red blood cells then can be directed to a red blood cell collection receptacle by operation of other electromechanically controlled clamps.

86 Claims, 6 Drawing Figures

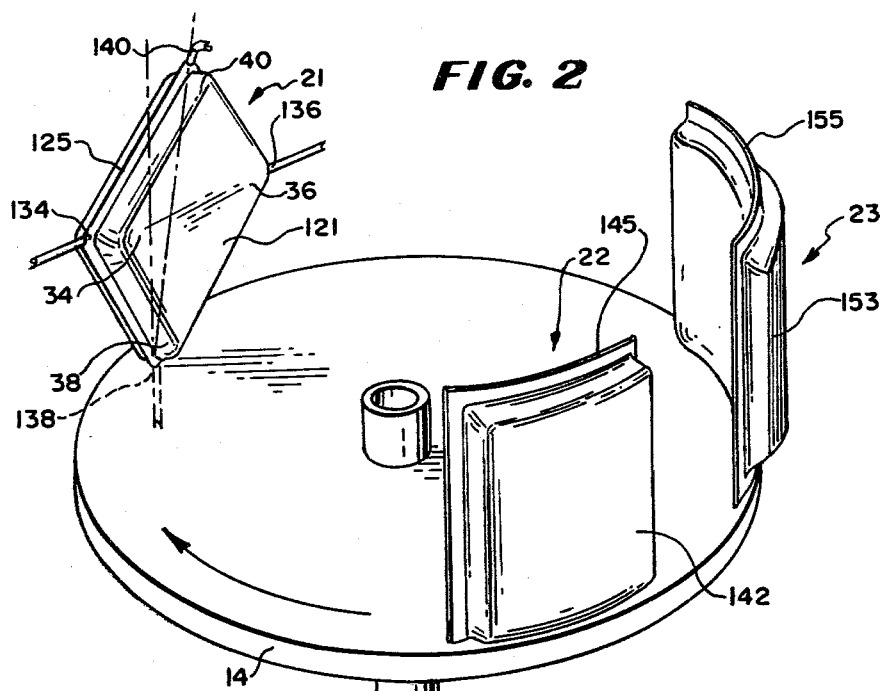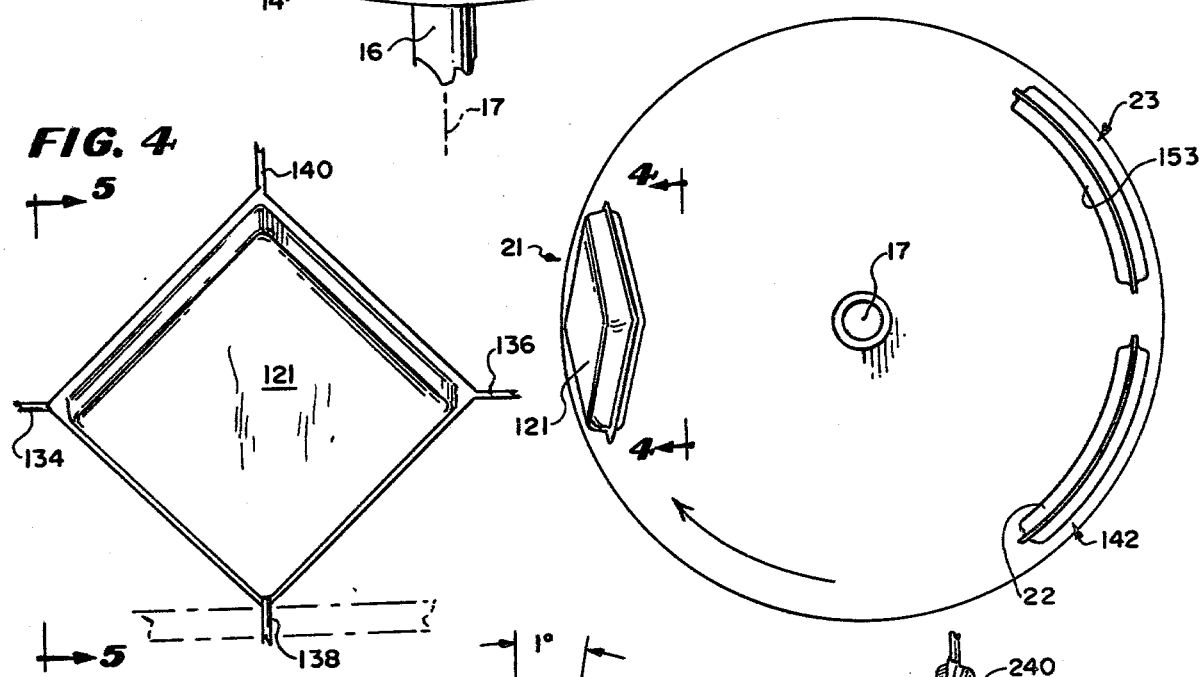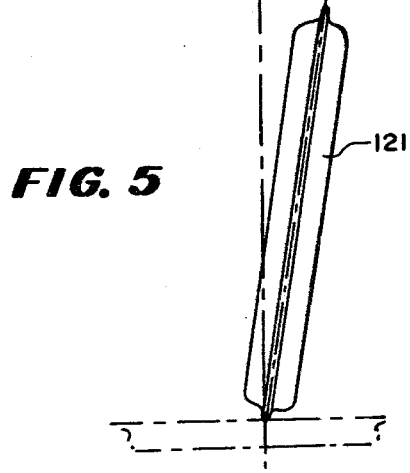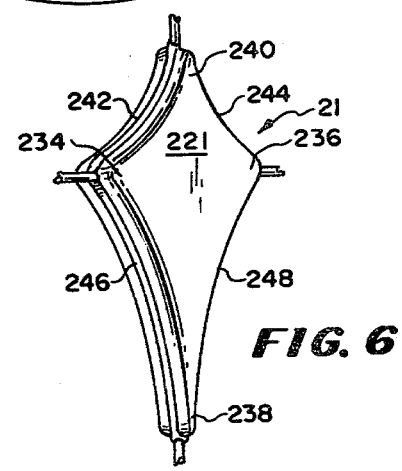

METHOD AND SYSTEM FOR FRACTIONATING A QUANTITY OF BLOOD INTO THE COMPONENTS THEREOF

CROSS REFERENCE TO RELATED APPLICATIONS

This application is related to and incorporates herein by reference, copending application Ser. No. 843,222 filed Oct. 18, 1977 and entitled: METHOD AND APPARATUS FOR PROCESSING BLOOD and copending application Ser. No. 843,296 filed Oct. 18, 1977 entitled: CENTRIFUGAL LIQUID PROCESSING SYSTEM.

BACKGROUND OF THE INVENTION

1. Field of the Invention

The present invention relates to a method and system for fractionating whole blood into its components and to a separation chamber within which blood is fractionated.

2. Description of the Prior Art

Heretofore, various methods and systems have been proposed for fractionating whole blood into the components thereof. Such prior art methods and systems have involved intervivos blood processing in which whole blood is taken from a live donor, separated within a processing system into its constituent components and a desired component (or components) is segregated for collection followed by returning the remaining blood fluid to the donor.

Whenever a live donor is supplying the blood to be fractionated there are always hazards involved and various protective steps have to be taken to insure that no harm comes to the donor. Examples of the various safeguards that need to be taken are explained in greater detail in the related co-pending application Ser. No. 843,222 referred to above. Also, in order to collect large numbers of white blood cells and platelets a healthy donor is usually required. This process for processing whole blood taken from a live donor is referred to as cytopheresis or plasmapheresis.

One previously proposed closed system for fractionating whole blood utilizes four plastic bags interconnected by plastic tubing. All the bags are placed in a centrifuge device and whole blood in a first bag is then centrifuged. Red blood cells collect at the bottom of the bag, white blood cells in the middle, and plasma collects at the top. A "plasma express" tubing which is closed inside is connected to the top of the bag and has an "in-line" cannula therein. After the first centrifuging, the cannula is moved in the tubing to open same and plasma and platelets are expressed from the first bag into a second bag by applying pressure to the first bag. Then the second bag is centrifuged to separate plasma from platelets and followed by expressing the platelets and plasma into respective third and fourth bags. This system requires operator intervention and takes several hours to complete. Also the efficiency of the separation is approximately 50%.

As will be described in greater detail hereinafter, the method and system of the present invention enables one automatically and efficiently to fractionate in a closed, sterile environment, previously collected stored quantities of whole blood or blood collected directly from a donor into the components thereof. It is estimated that by utilizing the blood fractionating method and system of the present invention, three pints of banked whole blood can be processed automatically in a closed sterile environment to produce quantities of the fractionated components thereof equivalent to the quantities of these components that would be obtained by extended cytopheresis or plasmapheresis and with an efficiency of fractionation of 90% or better.

Another advantage of the blood fractionating method and system of the present invention is that a donor can supply quantities or whole blood at different times, i.e., in batches—pints of whole blood stored in blood bags, and then each whole blood bag can be processed by the method and system of the present invention at any desired time without requiring a donor to be connected to the apparatus.

Also, and as will be explained in greater detail hereinafter, a further advantage of the method and system of the present invention is that any given quantity of whole blood can be more completely and better utilized by dividing it into desired components and distributing the components to different recipients. The economy arises because any given transfusion is made for the purpose of replenishing a single component, for example only red blood cells are needed, and the other components such as white blood cells, platelets and plasma will not generally contribute to the treatment and many times are injurious by virtue of their volume, particularly in the case of plasma, or by virtue of their incompatible antigenic nature, particularly in the case of white blood cells. Also, infusion of any blood component not actually required by the recipient is a waste of a vital and hard to obtain resource.

Moreover, as will be explained in greater detail hereinafter, the present system provides for the removal of certain plasma proteins, in particular, Immunoglobulin A, by removing the plasma and washing the red blood cells. In other words, removal of the plasma from the red cells removes Immunoglobulin A which has been shown to sensitize recipients and can be a cause of transfusion reactions. Sensitizing is a biological description of the process whereby an individual recognizes an antigen and gets an immune response, such as with allergies or hay fever.

SUMMARY OF THE INVENTION

According to the invention there is provided a method for fractionating a given amount of whole blood into several of its components, including the steps of: separating the whole blood in a chamber, such as by centrifugation, into at least one cellular portion and a primarily fluid portion; withdrawing the primarily fluid portion from the chamber; passing the primarily fluid portion back through the one separated cellular portion in the chamber at least once; and then removing the primarily fluid portion from the chamber thereby to effect a more complete separation of the primarily fluid portion from the one cellular portion of the blood.

Also according to the invention there is provided a method for fractionating a given amount of whole blood into components thereof and for collecting at least one cellular component, comprising the steps of supplying the whole blood to a first separation chamber mounted in a centrifuge device, centrifuging the whole blood in the first separation chamber and to cause fractionation fractionation of the whole blood into components thereof and to cause the components to congregate at different zones in the first separation chamber during centrifugation, withdrawing a first cellular component of the blood from the separation chamber and recirculating that first component back through the first separation chamber with the whole blood until only the first component is being recirculated, withdrawing blood fluid containing plasma, and apssing that blood fluid back into the first separation chamber in a direction which traverses the flow path of whole blood into, and withdrawal of the first component from the first separation chamber in a predetermined number of times thereby to elute blood components other than the first cellular component from the whole blood and first component with the blood fluid and to wash the first component with the blood fluid.

Further according to the invention there is provided a system for automatically fractionating a given quantity of whole blood into components thereof and for collecting at least one component comprising: a centrifuge device, a first separation chamber mounted in said centrifuge device and having first and second inlets and first and second outlets, means for withdrawing whole blood from a source thereof and for supplying same to said first inlet of said first separation chamber, first conduit means for coupling said first outlet of said first separation chamber to the source for recirculation, fluid coupling means for coupling said second outlet of said first separation chamber to said second inlet of said first separation chamber and means for causing blood fluid to flow from said second outlet to said second inlet and through said first separation chamber, and said inlets and outlets of said first separation chamber being arranged so that blood fluid flowing in said first separation chamber from said second inlet to said second outlet traverses the flow path of whole blood entering said first inlet and the blood component exiting from said first outlet such that the flowing blood fluid elutes blood components from the whole blood while at the same time the flowing blood fluid washes the one component.

Still further according to the invention there is provided for use in a blood fractionating system wherein whole blood is passed into and through a separation chamber in a centrifuge device for fractionating the whole blood into components thereof, an improved separation chamber having four corners and adapted to be positioned in a diamond position so that the four corners define an upper corner, a lower corner, a first side corner and a second side corner, said upper corner having an outlet for blood fluid containing components being fractionated in said separation chamber, said lower corner having a re-entry inlet for blood fluid withdrawn from said upper corner, said first side corner having an inlet for the whole blood and said second side corner having an outlet for a blood component.

BRIEF DESCRIPTION OF THE DRAWINGS

FIG. 2 is an enlarged perspective view of a portion of the centrifuge device utilized by the system 10 and shows the position of the separation chamber defined by plastic bags within the centrifuge device.

FIG. 3 is a top plan view of the plastic bags in the centrifuge device shown in FIG. 2.

FIG. 4 is a vertical elevational view of one side of the first separation chamber and is taken along line 4—4 of FIG. 3.

FIG. 5 is an edge view of the first separation chamber and is taken along line 5—5 of FIG. 4.

FIG. 6 is a vertical elevational view of a modified embodiment of the first separation chamber shown in the previous figures.

DESCRIPTION OF THE PREFERRED EMBODIMENT

Figure 1:
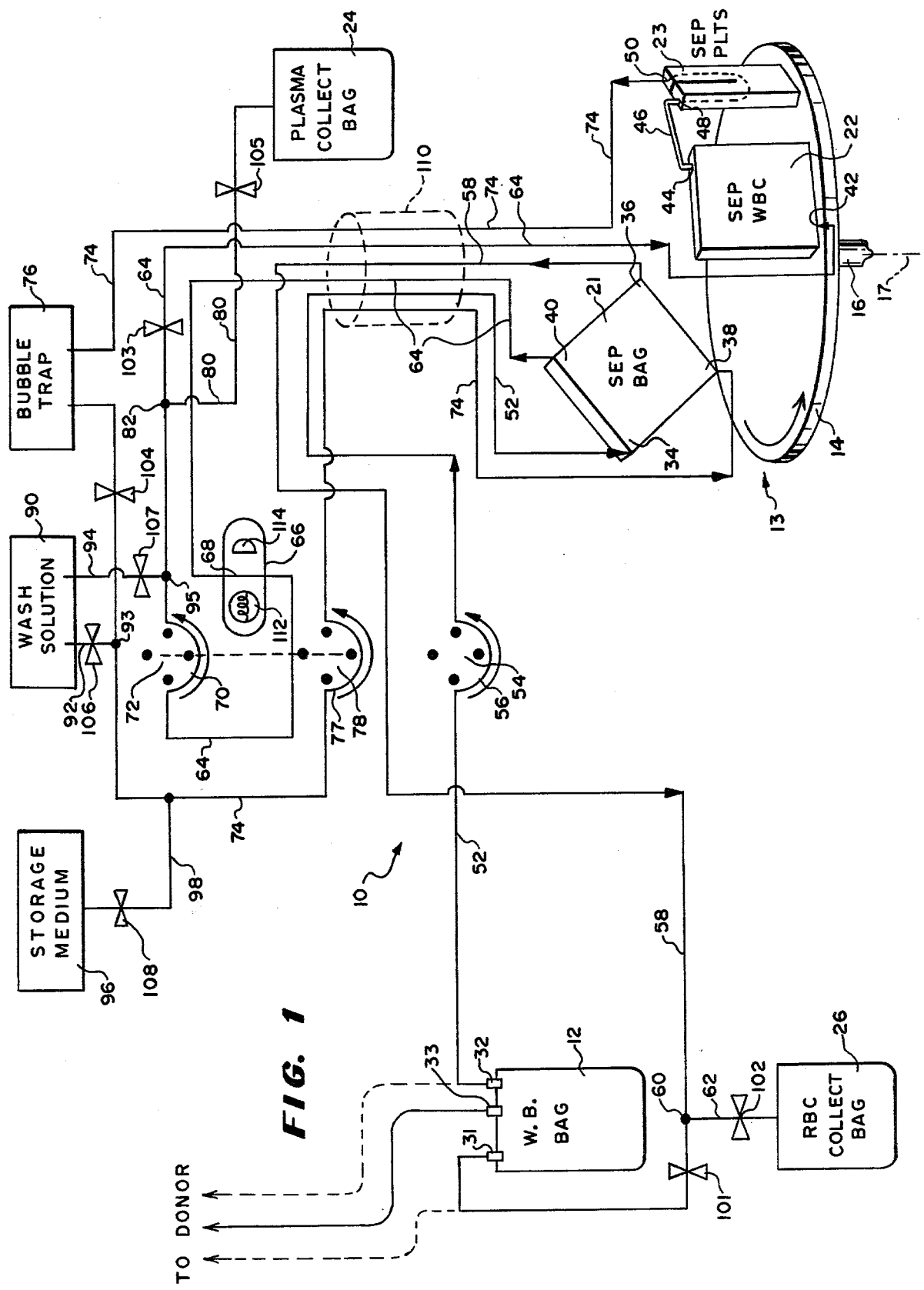
FIG. 1 is a schematic fluid circuit diagram of the blood fractionating system of the present invention.

Referring now to the drawings in greater detail, there is illustrated schematically in FIG. 1, the system of the present invention, generally identified by reference numeral 10, for fractionating whole blood obtained from a banked or stored container or bag 12 of whole blood into the components of the blood, namely red blood cells, white blood cells, platelets and plasma.

The system 10 includes a centrifuge device 13 which is schematically represented by a disc 14 mounted for rotation on a shaft 16 having an axis of rotation 17. Further details of construction of the centrifuge device 13 can be found in co-pending applications (1) Ser. No. 843,222 entitled METHOD AND APPARATUS FOR PROCESSING BLOOD and (2) Ser. No. 843,296 entitled CENTRIFUGAL LIQUID PROCESSING SYSTEM, the disclosures of which are incorporated herein by reference. Mounted in the centrifuge device 13 is a first separation chamber 21, a second separation chamber 22 and a third separation chamber 23. As will be described in greater detail hereinafter, the first separation chamber 21 is the primary separation chamber where the whole blood is fractionated or separated into red blood cells and plasma containing white blood cells and platelets. The second separation chamber 22 is utilized for separating white blood cells from plasma by means of centrifugation and sedimentation. The third separation chamber 23 is utilized for separating platelets from plasma by means of centrifugation and sedimentation.

The system 10 further includes a plasma collection receptacle or bag 24 and a red blood cell collection receptacle or bag 26.

As shown, inlet and outlet fittings or connections 31 and 32 are provided in the whole blood bag 12. It is to be understood that, if desired, blood can be collected directly from a donor and processed by the system 10. One way of doing this is to have another fitting 33 in the whole blood bag 12. As shown, this fitting 33 is connected to a line which is connected to a donor. When collecting blood directly using the donor line and fitting 33, fitting 33 is open to allow blood to bleed into the bag 12. Also, the bag 12 initially is filled with an anticoagulant and fittings 31 and 32 are closed and have in-line cannulas which can be moved to open them.

To obtain a fresh supply of whole blood, the donor line is connected to a donor and a quantity of blood is bled into the bag 12. Then the donor line is cut and sealed such as by an R.F. heat sealing device. Then the in-line cannulas are moved to open fittings 31 and 32 and the whole blood in the bag 12 is ready to be processed.

As shown, the first separation chamber 21 has a generally square or diamond shape and is situated in a diamond position within the centrifuge device 13. Positioned in this manner, the first separation chamber 21 has a first side corner 34, an opposite second side corner 36, a lower corner 38, and an upper corner 40. As will be described in greater detail in connection with the description of FIG. 4, the corners 34–40 each have openings for receiving conduits, (e.g.) plastic tubings.

As indicated in FIG. 1 the second separation chamber has a lower inlet 42 and an upper outlet 44. The upper outlet 44 is connected by a short conduit 46 to an upper inlet 48 of the third separation chamber 23 which also has an upper outlet 50.

The system 10 further includes a plurality of conduits defined below, which are typically flexible transparent plastic tubings. A first such conduit 52 couples the outlet 32 from the whole blood bag 12 to the first inlet at the first side corner 34 of the first separation chamber 21 and through a peristaltic pump 54. A portion 56 of conduit 52 is received in and forms part of the pump 54. A second conduit 58 is connected between a first outlet at the opposite side corner 36 of the first separation chamber 21 to the inlet 31 to the whold blood bag 12. Also, as shown, the second conduit 58 has a junction 60 therein and a third conduit 62 is connected to the junction 60 for the purpose of coupling the second conduit 58 to the red blood cell collection bag 26. A fourth conduit 64 is connected to a second outlet at the upper corner 40 of the first separation chamber 21 and extends out of the centrifuge device 13 and through a monitoring and sensing device 66 which is associated with a light transmitting portion 68 of the fourth conduit 64. Another portion 70 of the fourth conduit 64 passes over and forms part of a peristaltic pump 72. From there, the fourth conduit 64 extends back into the centrigude device to the lower inlet 42 of the second separation chamber 22. As explained above, the outlet 44 from the second separation chamber 22 is coupled by a short conduit 46 to the third separation chamber 23 and the outlet 50 thereof is coupled to a fifth conduit 74 which extends back out of the centrifuge device 13 and through a bubble trap 76. Then a portion 77 of the fifth conduit 74 extends over and forms part of another peristaltic pump 78 which is operated in tandem and in synchronization with the peristaltic pump 72. The fifth conduit 74 extends back into the centrifuge device to the second inlet at the lower corner 38 of the first separation chamber 21.

A sixth conduit 80 extends between a junction 82 in the fourth conduit 64 and the plasma collection bag 24. The junction 82 is located in the fourth conduit 64 between the portion 70 thereof and the inlet 42 to the second separation chamber 22.

It is to be understood that, if desired, the conduits 52 and 58 could be connected directly to a donor (as indicated by the phantom lines in FIG. 1) with, of course, safety devices in the conduits and a source of anticoagulant coupled to conduit 52 as explained in copending application Ser. No. 843,222 entitled METHOD AND APPARATUS FOR PROCESSING BLOOD.

Also, if desirable and as shown in FIG. 1, a source 90 of wash solution, such as saline solution, can be connected by a seventh conduit 92 to a junction 93 in the fifth conduit 74 between the portion 77 thereof and the bubble trap 76 and by an eighth conduit 94 to a junction 95 in the fourth conduit 64 between the portion 70 thereof and the junction 82.

In one preferred embodiment of the system 10 and as illustrated in FIG. 1, a source 96 of liquid, referred to herein as a storage medium, is coupled via a ninth conduit 98 to the fifth conduit 74 between junction 93 and pump 78. The storage medium is a liquid, e.g., water, containing dextrose and a saline solution. As will be explained in greater detail hereinafter the storage medium can be added to the red blood cells collected to add nutrients to them and give them more "body" or a "coating" to protect them from damage.

For controlling the various phases of operation of the blood fractionating system 10, the system 10 is provided with a plurality of valving devices which are realized by electromechanically controlled clamps associated with the conduits and which will be referred to hereinafter simply as valves. Each clamp, referred to herein as a valve, is situated on a piece of tubing for opening and closing fluid flow through the tubing and is not invasive of the closed system 10. These valves (clamps) are positioned as follows: A first valve 101 is associated with the second conduit 58 between junction 60 and inlet 31 to the whole blood bag 12. A second valve 102 is associated with the third conduit 62 between the junction 60 and the red blood cell collection bag 26. A third valve 103 is associated with the fourth conduit 64 between the junction 82 and the inlet 42 to the second separation chamber 22. A fourth valve 104 is associated with the fifth conduit 74 between the bubble trap 76 and the junction 93. A fifth valve 105 is associated with the sixth conduit 80 between the junction 82 and the plasma collection bag 24. A sixth valve 106 is associated with the seventh conduit 92 between the source 90 of wash solution and the junction 93 in the fifth conduit 74. A seventh valve 107 is associated with the eighth conduit 94 between the source 90 of wash solution and the junction 95 in the fourth conduit 64. And an eighth valve 108 is associated with the ninth conduit 98 between the storage medium source 96 and the fifth conduit 74.

Briefly summarizing the operation of the system 10, the processing of blood therein takes placed in a closed, aseptic environment. As shown, a supply of blood drawn from a donor or a previously banked supply of blood in the blood bag 12 is connected to the system 10. Then the pumps 54, 72 and 78 are operated with the pump 54 operating at roughly a fixed ratio of 3:1 to the speed of the pumps 72 and 78 which are operated in tandem. Whole blood is then pumped into the side corner 34 of the first separation chamber 21 which, by its configuration and orientation as will be described in greater detail in connection with the description of FIGS. 2-6, causes plasma, white blood cells and platelets to congregate at the upper corner 40 while red blood cells will congregate at the opposite side corner 36. The red blood cells congregating at the side corner 36 are caused to flow in the second conduit 58 by operation of the pump 54 to bring the red blood cells back into the whole blood bag 12. At this time, of course, first valve 101 is open and second valve 102 is closed. Meanwhile the centrifuge device 13 is rotating and the whole blood is being fractionated in the first separation chamber 21. The blood fluid, namely plasma containing white blood cells and platelets, at the upper corner 40 is withdrawn from the first separation chamber 21 by pump 72 and fed into the bottom of chamber 42. Also, of course, at this time valves 105, 106, 107 and 108 are closed and valves 103 and 104 are open.

Incidentally, the various conduits 52, 58, 64 and 74 that extend out of the centrifuge device are received through a larger tubing 110, a portion of which is shown by phantom lines. The larger tubing 110 is prevented from twisting while the centrifuge device 13 is rotating by means of rotating a holder for the tubing 110 at a different speed of rotation than the centrifuge device 13. This technique is explained in greater detail in co-pending application Ser. No. 843,222 entitled METHOD AND APPARATUS FOR PROCESSING BLOOD and obviates the need for fluid seals such that a completely closed system is obtained.

The pump 72 now pumps plasma with white blood cells and platelets through the conduit 64 and into the lower inlet 42 of the second separation chamber 22 which functions as a white blood cell separation chamber. Here, by means of the centrifugal force acting on the white blood cells and forcing them against the outer sidewall of the chamber 22, the white blood cells are separated from the platelets and sediment against the outer wall of the chamber 22 and the plasma flows out of the outlet 44 and into the conduit 46 through the platelet separation chamber 23. In this chamber 23 the platelets and plasma are caused to flow through a U-shaped path while undergoing centrifugation—the plasma flowing downwardly and then upwardly out the outlet 50. As a result of this flow path, the platelets are urged against the outer sidewall of the third separation chamber 23 and sediment out of the plasma. The plasma is then withdrawn through the fifth conduit 74 by means of the pump 78 and returned to the second inlet at the lower corner 38 of the first separation chamber 31.

As a result of the operation of the pumps 72 and 78, blood fluid rich in plasma and low in white blood cells and platelets flows across the first separation chamber 21 from the lower corner 38 to the upper corner 40 while whole blood flows across the first separation chamber 21 from the side corner 34 to the side corner 36. In this way, the plasma flow crossing the whole blood flow will elute the white blood cells and platelets from the whole blood and at the same time the plasma will wash the red blood cells. After this operation has taken place for a period of time, essentially only plasma is being passed vertically through the first separation chamber 21 and essentially only red blood cells are passed horizontally through the first separation chamber.

The fluid path for the plasma between the second outlet at the upper corner 40 and the second inlet at the lower corner 38 has a given volume and 3 to 8 of such volumes of plasma are circulated through the first separation chamber 21 during the processing of the given amount of whole blood in the blood bag 12. Preferably, 5 of these given volumes of plasma are passed through the first separation chamber 21 during processing of the given amount of whole blood. Also at the same time at least 3 volumes, e.g., pints, of whole blood are passed through the first separation chamber during processing of the given amount, e.g., pint of whole blood.

At this point in time the valve 103 will be closed and the valve 105 opened to collect plasma in the plasma collection bag. Then valve 101 is closed and valve 102 is opened to collect red blood cells.

Plasma is collected from conduit 64 after exiting from the upper corner of the separation chamber 21 and after having been recirculated through the first separation chamber 21 several times. However, plasma can be collected at a different point in the fluid circuit, e.g., after the plasma has passed through the three separation chambers 21, 22 and 23, by connecting the conduit 80 to the conduit 74 at the outlet side of pump 78. When connected in this manner, another valve (electromechanically operated clamp) is associated with the conduit 74 between the junction of the conduit 80 with the conduit 74 at the outlet side of the pump 78 and before the conduit 74 passes through the larger tubing 110. When it is desired to collect plasma, the additional valve is closed and valve 105 is opened. Although another valve is required, this arrangement may be desired for collecting plasma which has no, or a low incidence of, white blood cells and/or platelets therein.

If it is desired to further wash the red blood cells before collecting same after the plasma has been collected, valves 103, 104 and 105 can be closed and valves 106 and 107 opened so that a wash solution can be passed through the first separation chamber to wash the red blood cells which after being washed several times by the wash solution, can then be collected in the red blood cell collection bag 26.

Once the red blood cells are washed, they are in an unprotected state. Accordingly, it is often desirable to add fluid to the red blood cells when collecting them. This can be easily accomplished by adding back some platelet-poor plasma to the red cells by opening valve 105, maintaining valves 106 and 107 closed, and holding open valves 104 and 103.

Alternatively, fluid from the storage medium source containing dextrose, saline solution and nutrients can be added to the red blood cells to give them some "body" or a "coating", i.e., protection. This is accomplished by closing or maintaining closed valves 106 and 104 and opening valve 108 for a short time.

The blood fluid monitoring and sensing device 66 includes a light source 112 and a photodetector 114 which are arranged on either side of the light transmitting portion 68 of the conduit 64. Since it is desired not to mix red blood cells with the blood fluid containing plasma, white blood cells and platelets, the sensing device 66 is operable to sense the presence of red blood cells mixed with the blood fluid. When this occurs, suitable controls are operated to stop operation of the pumps 72 and 78 and to reverse operation of these pumps 72 and 78 for a predetermined period of time sufficient to return the RBC contaminated blood fluid (plasma) to the first separation chamber 21 for reseparation of the blood components. Then the control circuitry will reverse the operation of pumps 72 and 78 to cause them to pump in the original direction, namely the direction indicated in FIG. 1, to continue the operation of the system 10. Further details on the manner in which this may be accomplished are disclosed in copending application Ser. No. 843,222 entitled: METHOD AND APPARATUS FOR PROCESSING BLOOD.

Various methods for fractionating blood can be practiced utilizing the system 10 and a number of these methods are described below:

(1) In the simplest method for fractionating blood using the system 10, a given amount of whole blood is supplied to the separation chamber 21 followed by centrifuging the whole blood in the chamber 21 to cause the whole blood to separate into red blood cells at the side corner 36 and below with white blood cells above the red blood cells and plasma at the upper corner 40. Then the plasma with platelets and white blood cells is circulated through the separation chamber 21. In practicing this simple method for fractionating blood, the second and third separation chambers 22 and 23 can be omitted with the fourth and fifth conduits 64 and 74 being replaced by one fluid coupling for coupling the second outlet at the upper corner 40 through the peristaltic pumps 72 and 78 to the second inlet at the lower corner 38. Also in this method for fractionating a given amount of whole blood, the whole blood can be placed in the separation chamber 21 before operating the system 10 or can be supplied from the whole blood bag 12 and recirculated through the chamber 21 with eventually only red blood cells collecting at the corner 36 being recirculated. The passing of the plasma with platelets and white blood cells will effect a more complete separation of the red blood cells from the whole blood and the red blood cells can then be collected.

(2) Further method steps include the steps of collecting the plasma, platelets and white blood cells in the plasma collection receptacle 24 and then passing wash solution through the chamber 21 to wash the red blood cells which are being recirculated through the separation chamber 21 followed by collecting the red blood cells in either the whole blood bag 12 or the receptacle 26.

(3) Still further method steps include the steps of returning the wash solution to the wash solution source 90 prior to collecting red blood cells and then adding a storage medium to the red blood cells when collecting the same.

(4) Another method includes the steps of supplying whole blood to the separation chamber 21, centrifuging the blood in the separation chamber 21, withdrawing plasma with some white blood cells and platelets from the chamber 21 and passing that plasma through the third chamber 23 to separate the platelets and white blood cells from the plasma by centrifugation and sedimentation in the third chamber 23 and then collecting the red blood cells with some white blood cells, the platelets with some white blood cells and the plasma with some white blood cells.

(5) A further step to this method defined in the previous paragraph (4) is to add wash solution prior to collecting red blood cells.

(6) A still further step to the method described in the last paragraph (5) is to add back some plasma to the red blood cells when collecting them to protect the red blood cells.

(7) An alternative step to the step described in the previous paragraph (6) is to add back some plasma to the red blood cells when collecting them.

(8) Still another method includes the steps for separating the red blood cells from the plasma and platelets and white blood cells as described in paragraph (1) above followed by passing the plasma with platelets and white blood cells through the second chamber 22 for separating white blood cells from the plasma and platelets and then collecting red blood cells with some plasma and some platelets, white blood cells and plasma with platelets.

(9) A further step to the method described in the previous paragraph (8) is to pass a wash solution through the chamber 21 after collecting the white blood cells and plasma with platelets to further wash the red blood cells.

(10) A still further step which can be added to the method described in the previous paragraph (9) is to add a nutrient or to add plasma with platelets to the red blood cells when collecting them after washing the red blood cells with the wash solution.

(11) A further, preferred method includes the steps of supplying a given amount of whole blood to the first separation chamber 21, centrifuging the whole blood in the chamber 21 to cause fractionation of the whole blood into components thereof and to cause the components to congregate in different zones in the first chamber 21 during centrifugation, withdrawing the red blood cells from the first outlet at side corner 36 and recirculating them back through the first separation chamber 21 by reintroducing them into the first inlet at the side corner 34 with the whole blood until only red blood cells are being recirculated, withdrawing blood fluid, plasma containing platelets and white blood cells, from the upper corner 40 and passing that blood fluid containing plasma with white blood cells and platelets through the second separation chamber 22 to separate white blood cells from the blood fluid by centrifugation and sedimentation and then passing the blood fluid exiting from the second chamber 22 into the third chamber 23 to separate platelets from the blood fluid by centrifugation and sedimentation and passing the remaining blood fluid, namely plasma, back through the separation chamber 21 by introducing the plasma into the lower corner 38 of the chamber 21 and recirculating the plasma vertically through initially whole blood and later through just the red blood cells being recirculated horizontally through the chamber 21 to elute other particles from the red blood cells. After three volumes of the whole blood path have been circulated through chamber 21 and three to eight, preferably five, volumes of the plasma path have been recirculated through the separation chamber 21, the red blood cells can then be collected in the receptacle 26 by closing valve 101 and opening valve 102 and plasma can be collected in receptacle 24 by closing valve 103 and opening valve 105.

(12) An additional step to the method described in the previous paragraph (11) is to add back some of the plasma to the separation chamber 21 as the red blood cells are being collected in the receptacle 26.

(13) A further step to add to the preceding step is to pass a wash solution through the chamber 21 before collecting red blood cells in the receptacle 26.

(14) Another step to add to the method described in the previous paragraph (13) is to add back plasma to the red blood cells in chamber 21 after washing them with the wash solution and prior to completing collection of the red blood cells in the receptacle 26.

(15) An alternative method step to the step described in the previous paragraph (14) is to add a storage medium instead of plasma to the red blood cells in the chamber 21 after they have been washed with the wash solution and prior to or during the collection of the red blood cells in the red blood cell collection receptacle 26.

In the schematic diagram illustrated in FIG. 1 it is to be noted that the various containers, receptacles, chambers, etc. are shown in vertical positions which are directly related to the actual preferred vertical positions of these chambers or containers. In this respect, it will be apparent that the storage medium source 96 and wash solution source 90 are preferably located above the centrifuge device 13 to facilitate gravity flow of fluid from the source 96 and 90 into the centrifuge 13.

It is to be understood that the various separation chambers 21, 22 and 23 are defined by plastic bags which are held within specially formed platens (not shown). Platens and bags of this type are disclosed in co-pending application Ser. No. 843,296 entitled CENTRIFUGAL LIQUID PROCESSING SYSTEM. With this construction and arrangement of the chambers 21–23, once the three plastic chamber-defining bags have been utilized for processing a pint of blood from a whole blood bag 12, bag 21 can be discarded and bags 22 and 23 stored for future use of the white blood cells and platelets, and a new set of interconnected plastic bags and plastic tubings can be inserted into the system 10, i.e., into the centrifuge device 13 thereof, for again carrying out the method of blood fractionation in the system 10 as described above.

As best shown in FIG. 2 the plastic bags can take the shape of plastic bags having parallel spaced walls with the edges sealed together to form a seam running along the edge of the parallel spaced walls. In this respect, the first separation chamber 21 is defined by a plastic bag 121 having spaced sidewalls and a seam 125 extending around the bag 121 and between the sidewalls. The corners of the bag 121, that is the corners 34, 36, 38 and 40 of the first separation chamber 21 defined by the bag 121, have tubing connections 134, 136, 138 and 140 sealed in openings formed in the seam at the corners of the bag 121 and between the opposite sidewalls thereof.

The bag 121 has a diamond or square shape as described above and is positioned in platens (not shown) in a diamond position as shown.

The second separation chamber 22 is defined by a plastic bag 142 having spaced sidewalls and a seam 145 extending along the edges and a seam between the sidewalls extending along the edges of bag 142. For convenience, the inlet 42 and outlet 44 are omitted from the view of bag 142 in FIGS. 2 and 3. As shown, the bag 142 has a generally curved, rectangular shape and is positioned in the centrifuge device 13 in platens (not shown) on a cylindrical envelope coaxial with the axis 17 of rotation of the centrifugal device 13.

In a similar manner, the third separation chamber 23 is defined by a plastic bag 153 which has spaced sidewalls and a seam 155 and which is received in and between platens (not shown) in the centrifuge device 13. The bag 153 is similar to the bag 142 except that it is provided with some form of partition means that extends part way down from the top of the center of the bag 153 so that platelets and plasma are caused to follow a U-shaped path through the bag 153. Again, for convenience, the inlet 48 and outlet 50 are omitted from FIGS. 2 and 3 and, as with bag 142, the bag 153 has a curved, generally rectangular shape and is positioned in the centrifuge device 13 on a cylindrical envelope coaxial with the axis 17 of rotation of the centrifuge device and adjacent to the bag 142.

As shown in FIGS. 2 and 3, the first separation chamber 21, bag 121, is tilted inwardly toward the axis of rotation of the centrifuge device 13. The angle of tilt can be from 0+ to 5 degrees. As best shown in FIG. 5, the angle of tilt is preferably 1 degree. With the bag 121 positioned in this manner, the lower corner 38 of the chamber 21 defined by bag 121 is at a greater radius from the axis 17 than is the upper corner 40. Also, and as best shown in FIG. 3, the side corners 34 and 36 are located at approximately the same radius from the axis 17 of the centrifuge device 13. In this way, when whole blood comes into the corner 34 the flow pushes the red blood cells to the side corner 36 and they are withdrawn therefrom. Then the plasma, which is lighter than the red blood cells will congregate at the shorter radius which is adjacent the upper corner 40 of the chamber 21. Platelets will congregate below the plasma with white blood cells, (buffy coat), congregating between the platelets and the red blood cells. Plasma, platelets and white blood cells are withdrawn from the second outlet at the corner 40 and processed in the manner described above.

A modified embodiment of the first separation chamber 21 is shown in FIG. 6 and comprises a kite shaped plastic bag 221. This modified kite shaped bag 221 has a generally kite shape with side corners thereof, 234 and 236, located closer to the upper corner 240 than the bottom corner 238. Also the side edges of the kite shaped bag 221 are curved. In this respect there are two upper curved edges 242 and 244, and two lower curved edges 246 and 248. These curved edges follow generally parabolic curves and the actual curves chosen are ones which follow the naturally occurring flow paths of the blood components as they are undergoing centrifugation within the bag 121 as it is tilted one degree from the vertical and toward the axis of rotation of the centrifuge device as described above. This bag provides a somewhat smoother flow of the blood components within the bag 221. In this respect, with straight edges between corners, so-called "dead places" are found in the chambers where blood flow does not necessarily occur. This can be a problem when working with fresh blood since when flow does not occur there is a tendancy of the blood to clot and aggregate. Thus, elimination of "dead places" improves the efficiency of separation. Also the curved edge blood bag 221 reduces the volume of the separation chamber 221 without sacrificing performance of the system.

From the foregoing description it will be apparent that the system 10 of the present invention, the methods for utilizing the system 10 and the separation chamber 21 provide a number of advantages some of which have been described above and others of which are inherent in the invention. Also, it will be apparent to those skilled in the art that obvious modifications can be made to the system 10 and the bag 21 or 221 without departing from the teachings of the invention. Accordingly, the scope of the invention is only to be limited as necessitated by the accompanying claims.

We claim:

1. A method for fractionating a given amount of whole blood into several of its components, including the steps of: separating the whole blood in a chamber, such as by centrifugation, into at least one cellular portion and a primarily fluid portion; withdrawing the primarily fluid portion from the chamber; passing the primarily fluid portion back through the one separated cellular portion in the chamber at least once; and then removing the primarily fluid portion from the chamber thereby to effect a more complete separation of the primarily fluid portion from the one cellular portion of the blood.

2. The method according to claim 1 wherein said one cellular portion is comprised of red blood cells.

3. The method according to claim 1 wherein the fluid of said primarily fluid portion is comprised of plasma.

4. The method according to claim 1 wherein said primarily fluid portion is recirculated back through said one separated cellular portion by withdrawing said fluid portion from the top of the chamber containing said one cellular portion and introducing said fluid portion back into the bottom of the chamber.

5. The method according to claim 1 wherein said one cellular portion is comprised of red blood cells and said primarily fluid portion is comprised of plasma.

6. The method according to claim 1 wherein said one cellular portion is comprised of red blood cells and said primarily fluid portion is comprised of plasma and platelets.

7. The method according to claim 1 wherein said one cellular portion is comprised of red blood cells and said primarily fluid portion is comprised of plasma containing platelets and white blood cells.

8. The method according to claim 1 wherein said one cellular portion is comprised of red blood cells and wherein said method further includes the steps of: collecting the primarily fluid portion after passing it through the one cellular portion several times; passing a wash solution through the red blood cells; collecting the wash solution; and, then collecting the red blood cells.

9. The method according to claim 8 wherein some of said primarily fluid portion is added back to the red blood cells when collecting them.

10. The method according to claim 9 wherein said primarily fluid portion is comprised of plasma.

11. The method according to claim 8 wherein a storage medium containing nutrients is added to the red blood cells when collecting them.

12. The method according to claim 1 wherein said one cellular portion is comprised of red blood cells and said primarily fluid portion is comprised of plasma containing platelets and white blood cells and wherein said method further includes the steps of recirculating the primarily fluid portion through the red blood cells a predetermined number of times, collecting the primarily fluid component; and collecting the red blood cells.

13. The method according to claim 12 including the further steps of passing a wash solution through the red blood cells prior to collecting the red blood cells.

14. The method according to claim 13 including the step of adding a storage medium containing a nutrient to the red blood cells when collecting the red blood cells.

15. The method according to claim 1 wherein said one cellular portion is comprised of red blood cells and said primarily fluid portion is comprised of plasma containing platelets and white blood cells and wherein said method further includes the steps of: separating platelets from the primarily fluid portion, such as by passing the one fluid portion through a separation chamber undergoing centrifugation, prior to passing the primarily fluid portion back through the red blood cells; passing the platelet-poor primarily fluid portion through the red blood cells a predetermined number of times; collecting the plasma with some white blood cells; collecting the platelets with some white blood cells; and collecting the red blood cells with some white blood cells.

16. A method for fractionating a given amount of whole blood into components thereof and for collecting at least one cellular component, comprising the steps of supplying the whole blood to a first separation chamber mounted in a centrifuge device, centrifuging the whole blood in the first separation chamber to cause fractionation of the whole blood into components thereof and to cause the components to congregate at different zones in the first separation chamber during centrifugation, withdrawing a first cellular component of the blood from the separation chamber and recirculating that first component back through the first separation chamber with the whole blood until only the first component is being recirculated, withdrawing blood fluid containing plasma, and passing that blood fluid back into the first separation chamber in a direction which traverses the flow path of whole blood into, and withdrawal of the first component from the first separation chamber a predetermined number of times thereby to elute blood components other than the first cellular component from the whole blood and first component with the blood fluid and to wash the first component with the blood fluid.

17. The method according to claim 16 wherein the given amount of whole blood is contained in a closed container and said method is performed in a completely closed environment.

18. The method according to claim 16 wherein said given quantity of blood is initially taken from a donor and banked in a sealed air-tight bag from which it is supplied to the first separation chamber.

19. The method according to claim 18 including the step of collecting the first component comprised of red blood cells in the blood bag.

20. The method according to claim 18 including the step of collecting the first component comprised of red blood cells in a receptacle.

21. The method according to claim 20 including the step of recirculating the first blood component back through the whole blood bag for a predetermined period of time to ensure that all of the whole blood has been processed in and through the first separation chamber followed by collecting the first blood component comprised of red blood cells in the receptacle.

22. The method according to claim 16 including the steps of monitoring the compoistion of the blood fluid being withdrawn from the first separation chamber and adjusting the rate of supplying whole blood from a whole blood source in response to the composition sensed.

23. The method according to claim 16 including the steps of passing the blood fluid through a second separation chamber undergoing centrifugation to separate a second cellular blood component from the blood fluid prior to passing the blood fluid back through the first separation chamber; withdrawing the remaining blood fluid from the second separation chamber; and, then passing that blood fluid back into the first separation chamber.

24. The method according to claim 23 including the steps of monitoring the composition of the blood fluid being withdrawn from the first separation chamber and adjusting the rate of supplying whole blood from a whole blood source in response to the composition sensed.

25. The method according to claim 23 wherein the step of monitoring the composition of the blood fluid being withdrawn from the first separation chamber is for the purpose of sensing red blood cells mixed with the blood fluid and includes the steps of: stopping and then reversing for a predetermined time period the flow of blood fluid from the first separation chamber when red blood cells are sensed in the blood fluid thereby to return the mixture of blood fluid and red blood cells to the first separation chamber for reseparation of the blood components therein; adjusting the rate of supplying whole blood to the first separation chamber and the rate of withdrawal of blood fluid from the first separation chamber in response to the sensing of red blood cells in the blood fluid; and reversing the flow of blood fluid so that it is again withdrawn from the first separation chamber to continue the processing of the whole blood.

26. The method according to claim 25 wherein the sensing of the composition of blood fluid being withdrawn from the first separation chamber is performed outside of the centrifuge device.

27. The method according to claim 25 wherein the ratio of the rate of supplying whole blood to the first separation chamber is maintained at a given ratio.

28. The method according to claim 27 wherein the ratio of the rate of supplying whole blood to the first separation chamber to the rate of withdrawal of blood fluid from the first separation chamber is approximately 3:1.

29. The method according to claim 23 wherein said second cellular component is comprised of platelets.

30. The method according to claim 23 wherein said second cellular component is comprised of white blood cells.

31. The method according to claim 23 including the step of coupling a third separation chamber between the outlet from the second separation chamber and the inlet to the first separation chamber and wherein the first blood component separated from the whole blood in the first separation chamber constitutes red blood cells, the second component separated in the second separation chamber by centrifugation and sedimentation constitutes white blood cells and a third component which is separated by centrifugation and sedimentation in the third separation chamber constitutes platelets.

32. The method according to claim 31 including the step of collecting plasma in a plasma collection receptacle after the blood fluid containing plasma has been passed through the separation chambers for a predetermined period of time.

33. The method according to claim 32 including the step of passing the blood fluid exiting from the third separation chamber through a bubble trap prior to its re-entry into the first separation chamber.

34. The method according to claim 31 including the steps of: blocking the flow of blood fluid to the second separation chamber and the flow of blood fluid from the third separation chamber into the first separation chamber; coupling the outlet and inlet for the blood fluid from and into the first separation chamber to a source of wash solution; recirculating the first blood component back through the first separation chamber; passing the wash solution through the first separation chamber for a predetermined period of time to wash the first blood component constituting red blood cells and then collecting the red blood cells in a receptacle.

35. The method according to claim 34 including the step of adding some of the plasma to the red blood cells when collecting them.

36. The method according to claim 34 including the step of adding a storage medium to the red blood cells when collecting them.

37. The method according to claim 16 wherein the fluid path for the blood fluid has a given volume and 3 to 8 of such given volumes of blood fluid are circulated through the first separation chamber during the processing of the given amount of whole blood.

38. The method according to claim 37 wherein approximately 5 given volumes of blood fluid are passed through the first separation chamber during processing of the given amount of whole blood.

39. The method according to claim 16 wherein at least 3 given volumes of whole blood are passed through the first separation chamber during the processing of the given amount of whole blood.

40. A system for automatically fractionating a given quantity of whole blood into components thereof and for collecting at least one component comprising: a centrifuge device, a first separation chamber mounted in said centrifuge device and having first and second inlets and first and second outlets, means for withdrawing whole blood from a source thereof and for supplying same to said first inlet of said first separation chamber, first conduit means for coupling said first outlet of said first separation chamber to the source of recirculation, fluid coupling means for coupling said second outlet of said first separation chamber to said second inlet of said first separation chamber and means for causing blood fluid to flow from said second outlet to said second inlet and through said first separation chamber, and said inlets and outlets of said first separation chamber being arranged so that blood fluid flowing in said first separation chamber from said second inlet to said second outlet traverses the flow path of whole blood entering said first inlet and the blood component exiting from said first outlet such that the flowing blood fluid elutes blood components from the whole blood while at the same time the flowing blood fluid washes the one component.

41. The system according to claim 40 wherein said source of whole blood is a closed container and said system processes blood in a completely closed system.

42. The system according to claim 40 wherein said source of whole blood is a donor.

43. The system according to claim 40 wherein said source of whole blood is a container for whole blood and said system includes an inlet and an outlet connected to said container.

44. The system according to claim 43 wherein said container has another inlet for bleeding blood into said container from a donor after which the said another inlet is sealed.

45. The system according to claim 43 including a receptacle for collecting red blood cells, second conduit means for coupling a junction in said first conduit means to said receptacle, said outlet from said container being coupled to said first inlet of said first separation chamber, first valve means associated with a portion of said first conduit means between said junction and said container for controlling fluid flow in said first conduit means and second valve means associated with said second conduit means for controlling fluid flow in said second conduit means whereby the first blood component constituting red blood cells exiting from the first outlet of said first separation chamber first can, by operation of said first and second valve means, be caused to flow back through said container and back into said first separation chamber and subsequently can, by further operation of said first and second valve means, by delivered directly to said red blood cell collection receptacle.

46. The system according to claim 45 wherein said first and second conduit means are flexible tubings and said first and second valve means are electromechanically controlled clamps associated with said respective flexible tubings.

47. The system according to claim 40 including means associated with said fluid coupling means for monitoring and sensing the composition of the blood fluid being withdrawn from said first separation chamber and for causing a predetermined quantity of blood fluid to be returned to the first separation chamber when red blood cells mixed with the blood fluid are sensed.

48. The system according to claim 48 wherein a light transmitting portion of said fluid coupling means is situated outside said centrifuge device and said means for monitoring and sensing the composition of the blood fluid withdrawn from said first separation chamber includes a light source and a photodetector associated with said light transmitting portion of said fluid coupling means.

49. The system according to claim 40 including a second separation chamber situated in said centrifuge device and having an inlet and an outlet and wherein said fluid coupling means includes second conduit means for coupling said second outlet of said first separation chamber to said inlet of said second separation chamber and third conduit means for coupling said outlet of said second separation chamber to said second inlet of said first separation chamber.

50. The system according to claim 49 including a third separation chamber coupled into said third conduit means in series with and between said outlet of said second separation chamber and said second inlet of said first separation chamber.

51. The system according to claim 50 wherein said third separation chamber is a platelet separation bag which has a curved, generally rectangular shape and which is positioned in said centrifugal device on a cylindrical envelope coaxial with the axis of rotation of said centrifuge device.

52. The system according to claim 49 including a bubble trap coupled into said third conduit means in series with and between said second separation chamber and said second inlet to said first separation chamber.

53. The system according to claim 49 including a plasma collection receptacle, fourth conduit means for coupling a junction in said second conduit means to said plasma collection receptacle, first valve means associated with said fourth conduit means between said junction and said plasma collection receptacle for controlling fluid flow in said fourth conduit means, and second valve means associated with said second conduit means for controlling fluid flow in said second conduit means and second inlet to said second separation chamber, said second valve means being operable to block flow of plasma from said second outlet of said first separation chamber to said inlet of said second separation chamber and the connection of said fourth conduit means and the opening of said first valve means then permitting flow of plasma to said plasma collection receptacle.

54. The system according to claim 53 wherein said source of whole blood, said red blood cell collection receptacle and said plasma collection receptacle are situated outside said centrifuge device and said first, second and third conduit means comprise flexible tubings which extend from said centrifuge device and are rotated at a speed different than the speed of rotation of said centrifuge device to prevent twisting of the tubings thereby to provide a closed fluid system.

55. The system according to claim 53 wherein said conduit means comprise flexible tubings and each of said valve means comprises an electromechanically controlled clamp associated with one of said tubings.

56. The system according to claim 40 including a source of wash solution, second conduit means for coupling said source of wash solution to said fluid coupling means, first valve means associated with said fluid coupling means for blocking flow of blood fluid through said fluid coupling means and through said first chamber and second valve means associated with said second conduit means for permitting flow of wash solution through said second conduit means to said fluid coupling means and through said first separation chamber.

57. The system according to claim 56 including a source of storage medium, third conduit means for coupling said source of storage medium to said fluid coupling means and third valve means associated with said third conduit means to permit flow of storage medium through said third conduit means to said first separation chamber.

58. The system according to claim 57 wherein said conduit means and said fluid coupling means are comprised of flexible tubings and each of said valve means comprises an electromechanically controlled clamp associated with one of said tubings.

59. The system according to claim 49 including first valve means associated with said third conduit means between said second separation chamber and said inlet to said first separation chamber for controlling fluid flow in said third conduit means, a source of wash solution having a first fluid connection to said third conduit means between said first valve means and said second inlet to said first separation chamber and having a second fluid connection to said second conduit means, second valve means associated with said first fluid connection for controlling fluid flow through said first fluid connection, third valve means associated with said second fluid connection for controlling fluid flow therethrough, and fourth valve means associated with said second conduit means for controlling fluid flow therethrough and connected between said second fluid connection to said second conduit means and said inlet to said second separation chamber.

60. The system according to claim 59 including a source of storage medium, fourth conduit means for coupling said storage medium source to said third conduit means and fifth valve means associated with said fourth conduit means for controlling flow of storage medium through said fourth conduit means to said first separation chamber.

61. The system according to claim 60 wherein said conduit means and said fluid connections comprise flexible tubings and each of said valve means comprises an electromechanically controlled clamp associated with one of said tubings.

62. The system according to claim 49 wherein said second and third conduit means each have a portion thereof situated outside said centrifuge device and said blood fluid flow causing means includes first and second peristaltic pumps operated synchronously in tandem, said first pump being associated with and including said portion of said second conduit means and said second pump being associated with an including said portion of said third conduit means.

63. The system according to claim 62 wherein said conduit means comprises flexible tubings which extend out of said centrifuge device and which are rotated at a different speed of rotation than said centrifuge device to prevent twisting thereby to provide a closed fluid system.

64. The system according to claim 49 wherein said second separation chamber is a curved, generally rectangular, white blood cell collection bag which is located in said centrifuge device on a cylindrical envelope coaxial with the axis of rotation of said centrifuge device.

65. The system according to claim 40 wherein said first separation chamber has four corners and is arranged in a diamond position within said centrifuge device so as to have an upper corner, a lower corner, a first side corner, and a second side corner, said upper corner having said second outlet for blood fluid, said lower corner having said second inlet for re-entry of blood fluid into said first separation chamber, said first side corner having said first inlet for whole blood and said second side corner having said first outlet for the one blood component.

66. The system according to claim 65 wherein said first separation chamber has spaced sidewalls which extend to each of said corners and has edges between said corners.

67. The system according to claim 66 wherein said first separation chamber is positioned in said centrifuge device with the radius from the axis of rotation of the centrifuge device to said upper corner being shorter than the radius from the axis of rotation of said centrifuge device to said lower corner.

68. The system according to claim 67 wherein said two side corners are each positioned respectively substantially the same radial distance from the axis of rotation of said centrifuge device.

69. The system according to claim 66 wherein said first separation chamber is positioned in the centrifuge device so that a plane extending between said upper and lower corners and including tangents at said corners is at an angle of between 0+ and 5 degrees to the vertical.

70. The system according to claim 69 wherein said angle is approximately 1 degree.

71. The system according to claim 65 wherein said first separation chamber has a generally square configuration.

72. The system according to claim 65 wherein said first separation chamber has a generally diamond configuration.

73. The system according to claim 65 wherein said first separation chamber has a general shape of a kite with said two side corners being closer to said upper corner than to said lower corner.

74. The system according to claim 73 wherein said edges of said first separation chamber extending between said corners thereof are concave.

75. The system according to claim 74 wherein said concave edges of said first separation chamber follow generally parabolic curves which are related to the parabolic flow paths of the blood components as they are being centrifuged in said first separation chamber.

76. For use in a blood fractionating system wherein whole blood is passed into and through a separation chamber in a centrifuge device for fractionating the whole blood into components thereof, an improved separation chamber having four corners and adapted to be positioned in a diamond position so that the four corners define an upper corner, a lower corner, a first side corner and a second side corner, said upper corner having an outlet for blood fluid containing components being fractionated in said separation chamber, said lower corner having a re-entry inlet for blood fluid withdrawn from said upper corner, said first side corner having an inlet for the whole blood and said second side corner having an outlet for a blood component.

77. The separation chamber according to claim 76 having spaced sidewalls which extend to each of said corners and edges between said corners.

78. The separation chamber according to claim 77 being adapted to be positioned in the centrifuge device with the radius from the axis of rotation of the centrifuge device to said upper corner being shorter than the radius from the axis of rotation of the centrifuge device to said lower corner.

79. The separation chamber according to claim 78 wherein said other two corners are each adapted to be positioned, respectively, at substantially the same radial distance from the axis of rotation of the centrifuge device.

80. The separation chamber according to claim 79 wherein said chamber is adapted to be positioned in the centrifuge device so that a plane extending between said upper and lower corners and including tangents at said corners is at an angle of between 0+ and 5 degrees to the vertical.

81. The separation chamber according to claim 80 wherein said angle is approximately 1 degree.

82. The separation chamber according to claim 76 having a generally square configuration.

83. The separation chamber according to claim 76 having a generally diamond configuration.

84. The separation chamber according to claim 76 having the general shape of a kite with said side two corners being closer to said upper corner than to said lower corner.

85. The separation chamber according to claim 84 wherein said edges of said separation chamber extending between said corners thereof are concave.

86. The separation chamber according to claim 85 wherein said concave edges of said chamber follow generally parabolic curves which are related to the parabolic flow paths of the blood components as they are being centrifuged in said chamber.

* * * * *